US011471432B2

(12) United States Patent
Gold et al.

(10) Patent No.: US 11,471,432 B2
(45) Date of Patent: *Oct. 18, 2022

(54) SUPPORTING IMMUNOMODULATORY AGENT

(71) Applicant: Flexopharm Brain GMBH & Go. KG, Herne (DE)

(72) Inventors: Ralf Gold, Bochum (DE); Aiden Haghikia, Bochum (DE); Ulrich Matthes, Herne (DE)

(73) Assignee: Flexopharm Brain GMBH & Co. KG, Herne (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/915,628

(22) Filed: Jun. 29, 2020

(65) Prior Publication Data
US 2020/0323802 A1  Oct. 15, 2020

Related U.S. Application Data

(63) Continuation of application No. 15/769,282, filed as application No. PCT/EP2016/066350 on Apr. 27, 2017, now Pat. No. 10,695,305.

(30) Foreign Application Priority Data

Feb. 24, 2016 (DE) ..................... 10 2016 103 242.5

(51) Int. Cl.
| | |
|---|---|
| A61K 31/19 | (2006.01) |
| A61K 31/215 | (2006.01) |
| A61K 31/25 | (2006.01) |
| A61P 17/06 | (2006.01) |
| A61P 37/02 | (2006.01) |
| A61K 31/714 | (2006.01) |
| A61K 9/20 | (2006.01) |
| A61K 9/48 | (2006.01) |
| A61K 31/225 | (2006.01) |

(52) U.S. Cl.
CPC ............ *A61K 31/19* (2013.01); *A61K 31/215* (2013.01); *A61K 31/25* (2013.01); *A61K 31/714* (2013.01); *A61P 17/06* (2018.01); *A61P 37/02* (2018.01); *A61K 9/20* (2013.01); *A61K 9/48* (2013.01); *A61K 31/225* (2013.01); *A61K 2300/00* (2013.01)

(58) Field of Classification Search
CPC ....................................................... A61K 31/19
See application file for complete search history.

(56) References Cited

U.S. PATENT DOCUMENTS

| | | | | |
|---|---|---|---|---|
| 4,959,389 A | * | 9/1990 | Speiser ................ | A61K 31/225 514/494 |
| 10,226,443 B2 | | 3/2019 | Scher et al. | |
| 10,682,322 B2 | * | 6/2020 | Gold ........................ | A23L 33/16 |
| 10,695,305 B2 | * | 6/2020 | Gold .................... | A61K 31/714 |
| 2007/0248662 A1 | | 10/2007 | Joshi et al. | |
| 2011/0033946 A1 | | 2/2011 | Berenson et al. | |
| 2011/0112010 A1 | | 5/2011 | Hallett et al. | |
| 2017/0231933 A1 | | 8/2017 | Gold et al. | |
| 2018/0214399 A1 | | 8/2018 | Spector et al. | |
| 2018/0303778 A1 | | 10/2018 | Gold et al. | |

FOREIGN PATENT DOCUMENTS

| | | |
|---|---|---|
| DE | 19503598 A1 | 8/1996 |
| FR | 2782608 A1 | 3/2000 |
| WO | 2010105112 A1 | 9/2010 |
| WO | 2017067681 A1 | 4/2017 |
| WO | 2018162698 A1 | 9/2018 |

OTHER PUBLICATIONS

Thacker et al., Effects of Vitamin B12 On Serum Lipids and Lipoproteins of Pigs Fed Diets Supplemented With Propionic Acid or Calcium Propionate, Canadian Journal of Animal Science, vol. 62 (2), Jun. 1982, 527-536.*
Duscha et al., Beneficial effects of short chain fatty acids on the course of experimental autoimmune encephalomyelitis, 143 vol. 275, Issue 1-2, p. 59, Oct. 15, 2014.*
Silfvast-Kaiser et al., A narrative review of psoriasis and multiple sclerosis: links and risks, Psoriasis (Auckl). 2019; 9: 81-90.*
Sampson TR et al., "Gut microbiota regulate motor deficits and neuroinflammation in a model of Parkinson's disease" Cells 2016, vol. 167, pp. 1469-1480.
St. Laurent R et al., "Sodium butyrate improves locomotor impairment and early mortality in a rotenone-Induced *drosophila* model of Parkinson's disease" Neuroscience 2013, vol. 246, pp. 382-390.
Lei E et al., "Fatty acids and their therapeutic potential in neurological disorders" Neurochemistry International 2016, vol. 95, pp. 75-84.
Non-Final Office Action for U.S. Appl. No. 16/627,688, filed Apr. 14, 2021.
Canani RB et al., "Potential beneficial effects of butyrate in intestinal and extraintestinal diseases" World J. Gastroenterol. 2011, vol. 17, No. 12, pp. 1519-1528.
Neesby TE "Neesby Butyrex (Butyric Acid, Butyrate) A Calcium Magnesium Butyrate Complex 600 mg 250 capsules" amazon.com, product first available date Oct. 2016. Downloaded from <https://www.amazon.com/Butyrex-Butyric-Butyrate-Magnesium-capsules/dp/B003JOJ04G/ref=sr_1_2?crid=1QWRMHKQDM2GQ&dchild=1&keywords%E2%80%A6>.
ClinicalTrials.gov, NCT02976688, last update posted Nov. 29, 2016.

(Continued)

*Primary Examiner* — Svetlana M Ivanova
(74) *Attorney, Agent, or Firm* — Wuersch & Gering LLP

(57) ABSTRACT

The invention relates to a combination therapy for the prevention and/or treatment of immune-mediated chronic inflammatory and autoimmune diseases comprising a combination of one or more $C_3$-$C_8$ carboxylic acids, physiologically acceptable salts and/or esters thereof, and one or more fumaric acid esters and/or salts thereof. The combination being particularly useful in the treatment of psoriasis and multiple sclerosis.

20 Claims, 6 Drawing Sheets

(56) References Cited

OTHER PUBLICATIONS

Armstrong MJ et al., "Diagnosis and Treatment of Parkinson Disease" JAMA 2020, vol. 323, No. 6, pp. 548-560.
SIGMA-ALDRICH Catalog "Sodium propionate" Catalog # P5436, retreived from Internet on Apr. 8, 2021. Downloaded from URL: <https://www.sigmaaldrich.com/catalog/product/sigma/p1880?lang=en&region=US>.
Unger MM., "Short chain fatty acids and gut microbiota differ between patients with Parkinson's disease and age-matched controls" Parkinsonism and Related Disorders 2016, vol. 32, pp. 66-72.
The Good Scents Company "ethyl 2-methyl butyrate" Apr. 3, 2016, retreived from Internet on Apr. 9, 2021. Downloaded from URL: https://web.archive.org/web/20160403214807/http://www.thegoodscentscompany.com/data/rw1004871.html.
Dajose L "Parkinson's Disease Linked to Microbiome" Caltech, Dec. 1, 2016. Retrieved from the internet; URL: <https://www.caltech.edu/about/news/parkinsons-disease-linked-microbiome-53109>.
Bourassa MW, et al. Butyrate, Neuroepigenetics and the Gut Microbiome: Can a High Fiber Diet Improve Brain Health? Neuroscience Letters 2016, vol. 625, pp. 56-63.
Unger MM, et al. "Short Chain Fatty Acids and Gut Microbiota Differ Between Patients with Parkinson's Disease and Age-Matched Controls" Parkinsonism and Related Disorders 2016, vol. 32, pp. 66-72.
Duscha A, et al. "Beneficial Effects of Short Chain Fatty Acids on the Course of Experimental Autoimmune Encephalomyelitis" Journal of Neuroimmunology, Oct. 15, 2014, vol. 275, No. 1 , p. 59 Abstract.
Smith PM, et al. "The Microbial Metabolites, Short Chain Fatty Acids, Regulate Colonic Treg Cell Homeostasis" Science ,Aug. 2, 2013, vol. 341, No. 6145, pp. 569-573.
Haghikia A, et al. "Impact of Fatty Acids on CNS Autoimmunity and Their Therapeutic Potential for Multiple Sclerosis" ECTRIMS Online Library, Oct. 7, 2015. Retrieved from the Internet; URL: http://citenpl.internal.epo.org/wf/web/citenpl/citenpl.html [Retrieved on May 17, 2017] abstract.

Furusawa Y, et al. "Commensal Microbe-Derived Butyrate Induces the Differentiation of Colonic Regulatory T Cells" Nature, Dec. 19, 2013, vol. 504, No. 7480, pp. 446-450.
Berg J, et al. "Beneficial Effects of Short Chain Fatty Acids on the Course of Experimental Autoimmune Encaphalomyelitis" Journal of Neuroimmunology Oct. 15, 2014, vol. 275, No. 1, p. 59.
Gross CC, et al. "Dimethyl Fumarate Treatment Alters Circulating T Helper Cell Subsets in Multiple Sclerosis" Neurology—Neruoimmunology NeuroInflammation, Dec. 10, 2015, vol. 3, No. 1, pp. e183, XP055312762.
Haghikia A, et al. "Session 042—MS and CNS Inflammatory Disease: Risk Factors in Multiple Sclerosis: Therapeutic Potential of Propionic Acid" AAN Meeting 2016, Apr. 16, 2016, pp. 1-1, XP055312758.
International Search report forms 210 and 237 (German and machine translation English) for PCT/EP2015/074179 dated Dec. 2, 2016.
Miller et al., "Clinical Pharmacology of Sodium Butyrate in Patients with Acute Leukemia," European Journal of Cancer and Clinical Oncology 1987, vol. 23, No. 9, pp. 1283-1287 (Abstract).
Thacker PA, et al. "Effects of Vitamin B12 on Serum Lipid and Lipoproteins of Pigs Fed Diets Supplemented with Proprionic Acid or Calcium Propionate" Canadian Journal of Animal Science 1982, vol. 62, pp. 527-536.
Berggren AM, et al. "Influence of Orally and Rectally Administered Propionate on Cholesterol and Glucose Metabolism in Obese Rats" British Journal of Nutrition 1996, vol. 76, pp. 287-294.
Venter CS, et al. "Effects of Dietary Propionate on Carbohydrate and Lipid Metabolism in Healthy" The American Journal of Gastroenterology May 1990, vol. 85, No. 5, pp. 549-553 (Abstract).
Lin By, et al. "Differences in Propionate-Induced Inhibition of Cholesterol and Triacylglycerol Synthesis Between Human and Rat Hepatocytes in Primary Culture" British Journal of Nutrition 1995, vol. 74, pp. 197-207.
Davidson MH, et al. "Efficacy and Tolerability of Atorvastatin/Fenofibrate Fixed-Dose Combination Tablet Compared With Atorvastatin and Fenofibrate Monotherapies in Patients with Dyslipidemia: A 12-Week, Multic-Center, Double-Blind, Randomized, Parallel-Group Study" Clinical Therapeutics 2009, vol. 31, No. 12, pp. 2824-2838.
Lucas S, et al. "Short-Chain Fatty Acids Regulate Systemic Bone Mass And Protect from Pathological Bone Loss" Nature Communications 2018, vol. 9:55, DOI: 10.1038/s41467-017-02490-4 | www.nature.com/naturecommunications.

* cited by examiner

SUPPORTING IMMUNOMODULATORY AGENT

CROSS REFERENCE TO RELATED APPLICATIONS

This application is a continuation of U.S. National Stage application 151769282, filed on Apr. 18, 2018, now U.S. Pat. No. 10,695,305, under 35 U.S.C. § 371 of PCT/EP2016/066350, filed on Apr. 27, 2017, which claims priority to PCT/EP2015/074179, filed on Oct. 19, 2015, and to DE 10 2016 103 242.5, filed on Feb. 24, 2016.

TECHNICAL FIELD

The invention relates to a combination therapeutic for use in the treatment of autoimmune diseases and immune-mediated chronic inflammatory diseases comprising administering one or more $C_3$-$C_8$ carboxylic acids and their physiologically acceptable salts and/or esters, and one or more fumaric acid esters and/or salts thereof. The combination is particularly effective for immunemediated diseases and irritations such as psoriasis, multiple sclerosis and neurodermatitis.

BACKGROUND

In autoimmune-related diseases the body's own tissues are targeted as a result of a dysfunctional immune response, for example in multiple sclerosis (MS) and in immune-mediated chronic inflammatory diseases that cause inflammation in various tissues, including the intestines (Crohn's disease, ulcerative colitis), in the skin (psoriasis) or of the joints (spectrum of rheumatic diseases). Common to all these disease conditions is that due to the inflammation other disease conditions may occur with an above-average frequency, such as excess weight, high blood pressure, arteriosclerosis, cardiac infarction, and stroke.

Recent knowledge gained in the field of microbiomes has shown that nutrition, the intestinal microbiome, and the local cellular immune response are interconnected. This suggests that dietary measures can have an influence on the cellular immune response and thus on the course of autoimmune diseases and immune-mediated chronic inflammatory diseases The diversity of the microbiome of the intestine plays an important role. Despite many unanswered questions concerning which components of the microbiome are actually responsible for a differentiated adaptive immune response in the intestinal region, a great amount of empirical information has been collected suggesting that individual types of bacteria and their bacterial metabolites exert a considerable influence on the systemic immune response in connection with autoimmune diseases and immune-mediated chronic inflammatory diseases, for example, in the case of 1 diabetes and Crohn's disease.

It has been found that the intestinal microbiome can be influenced by the type of nutrition consumed and is able to adapt to conditions created by a given kind of food. This means that an intestinal microbiota unfavorable to the immune status of a patient can be changed by taking suitable dietary measures aimed at improving the immune status of the patient.

The intestinal microbiome and dietary habits, such as a high salt intake, have recently been identified as environmental factors in the pathogenesis of multiple sclerosis (MS), an example of an autoimmune-related disease of the central nervous system mediated by T cells. The influence of the intestinal microbiome on chronic inflammatory diseases of the intestines and type 1 diabetes was mentioned above. Distinctive characteristics of the intestinal microbiota have also been detected in patients suffering from type 2 diabetes. Additionally, an association with neurodegenerative diseases (Parkinson's Alzheimer's) has also been suggested. Recent evidence also shows that there is a major alteration of the intestinal microbiome in the event of renal insufficiency.

An essential role in-autoimmune diseases and in immune-mediated chronic diseases is the action of regulatory T cells (Treg). Treg cells, also known as suppressor T cells, control the activity of the immune system. A deficiency of Treg cells is associated with numerous autoimmune diseases.

Fatty acids have a major influence on the intestinal microbiome as well as on regulatory T cells. It has been reported that long-chain fatty acids have proinflammatory activity. It has now surprisingly been found that short-chain fatty acids have a positive effect on the proliferation and amount of regulatory T cells. This was particularly the case for propionic and butyric acid and their physiologically acceptable salts and esters. Moreover, it has been determined that the targeted administration of short-chain fatty acids with three to six carbon atoms has a positive influence on the development and progression of neuroimmunological diseases with neurodegenerative aspects, like MS.

The use of fumaric acid esters and salts, in particular dimethyl fumarate and salts of monomethyl fumaric acid, for the treatment of MS and psoriasis has been known for years. These agents are effective, but their administration at the threshold of effectiveness is associated with unpleasant side effects, such as gastrointestinal problems and reddening of the skin. The gastrointestinal problems seem to be associated with irritation of the gastric mucosa. In addition, the use of fumarates is associated with leukopenia.

Fumarates are administered—primarily as dimethyl fumarate—in daily doses of usually 2×120 mg (starting dose) or 2×240 mg (maintenance dose). In individual cases a higher dose may be required. Patient doses are often individually adjusted. In MS therapy, dimethyl fumarate is administered as a monotherapy, in psoriasis therapy fumarates are administered as a combination preparation in daily doses of 100 mg to 1.2 g.

SUMMARY OF THE INVENTION

The invention is based on the finding that short-chain fatty acids are conducive to significantly increasing the amount of Treg cells in the short term when administered in combination with fumarates. The increase in Treg cells is much greater for fumarates than for other drugs approved for the treatment of MS.

Accordingly, the invention relates to a combination preparation for use in the prophylaxis and therapy of immune-mediated chronic inflammatory and autoimmune diseases, comprising a combination of $C_3$-$C_8$ fatty acid, physiologically tolerable salts and/or esters thereof and one or more fumaric acid esters and/or their physiologically acceptable salts thereof.

DETAILED DESCRIPTION OF THE INVENTION

Figure 1:
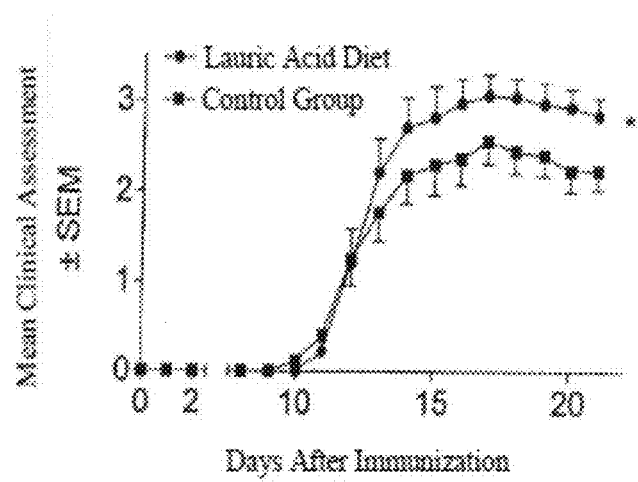
FIG. 1 is a graph showing the results of a study comparing the effect of a lauric acid diet compared to a control group on SEM clinical assessments in a mouse experimental autoimmune encephalomyelitis (EAE) model.

Autoimmune-related diseases referred to here are primarily those whose development is associated with abnormalities in the intestinal microbiota and in the occurrence of regulatory T cells. For example, these include neurodegenerative diseases such as MS or other autoimmune-related disease such as psoriasis, inflammatory bowel disease (IBD), rheumatoid arthritis and the various types of diabetes.

The inventive effect is limited to short-chain carboxylic acids, i.e. those with no more than eight carbon atoms. With longer chained carboxylic acids opposite effects are observed. Carboxylic acids with twelve or more carbon atoms usually exert a negative effect on the development and progression of the disease.

Especially preferred $C_3$-$C_8$ carboxylic acids are propionic acid and butyric acid as well as their salts and esters.

The term carboxylic acids is understood to mean monocarboxylic acids preferably of the straight-chain configuration. The monocarboxylic acids may also contain double bonds. However, preferred are straight-chained saturated carboxylic acids, in particular those with three or four carbon atoms.

The alkali and alkaline earth metal salts are most preferable as physiologically acceptable salts. Additionally, salts of physiologically safe or essential heavy metals, for example zinc or iron can be used. Of the alkali metals, sodium and potassium are especially preferred, as are magnesium and calcium of the alkaline earth metals.

Regarding esters, preference is given to methyl and ethyl esters.

The short-chain fatty acids and their esters and salts are combined with fumaric acid esters and their salts. The active substances can be administered as a combination preparation, but also separately.

Dimethyl fumarate is particularly suitable as a fumaric acid ester, but other fumarate esters with $C_{1-6}$ alcohols may also be used. Diesters are preferred, but salts of the monoester can also be used, in particular the alkali and alkaline earth metal salts as well as zinc and iron salts. Aside from sodium and potassium salts, in particular the calcium salt, magnesium salt and zinc salt are preferred.

A mixture of dimethyl fumarate and the calcium, magnesium and zinc salts of ethyl fumarate is also particularly suitable as a fumaric acid component. Such a mixture is used in dermatology for the treatment of psoriasis.

For short-chain fatty acids and their salts or esters, the maximum daily dose is up to 10 g, preferably up to 5 g. Typically, doses ranging between 0.5 g and 1.5 g per day are sufficient, for example in the form of two administrations of 0.5 g in the morning and evening. For example, one capsule or tablet may contain 0.5 g sodium propionate or calcium propionate.

The typical daily dose of fumarates is 2×120 mg or 2×240 mg in tablet or capsule form. However, using the inventive combinations with fumarates enables the maximum daily dose of the fumarate to be reduced to about half those stated above which reduces side effects.

The short-chain carboxylic acids of the invention and their esters and salts may be combined with other active agents as well as with vitamins, in particular with vitamins A, B12 and/or D.

In the invention, vitamin B12 refers to all compounds of the vitamin B12 group, i.e. cobalamins and in particular cyanocobalamin and storage forms of vitamin B12 as well as coenzyme B12.

Vitamin B12 has been shown to be effective in a number of diseases associated with immune system disorders such as MS, psoriasis and neurodermatitis. It is involved in the total fat metabolism. An incorrect colonization of the intestine can lead to a vitamin B12 deficiency.

A combination of fatty acids with vitamin B12 and preferably also vitamin D has proven to be beneficial. Vitamin B12 also promotes the resorption of short-chain fatty acids, such as propionic acid and sodium propionate.

The vitamin B12 content is based on the recommended dose, a maximum of 5 μg per day.

The inventive combination preparation may be provided in any marketable form. Preferred forms are capsules and tablets. The short-chain fatty acids in the form of solid salt, sodium propionate or calcium propionate, may be compressed into tablets using customary tableting means. If odor-intensive short-chain fatty acids and their salts and esters are used, odor-binding substances such as cyclodextrins can be admixed.

The individual active ingredients of the combination preparation proposed by the invention may be present together, i.e. in a capsule or tablet, or may be separately encapsulated or tableted. A suitable form for the daily administration is the introduction of the daily dose of the active substances, separately encapsulated, in a blister pack. For example with two capsules of sodium or calcium propionate of 0.5 g each and one capsule or tablet of dimethyl fumarate of 120 mg or 240 mg. In this case, any vitamin supplements, in particular vitamin B, are added to the fatty acid salt.

Figure 6:
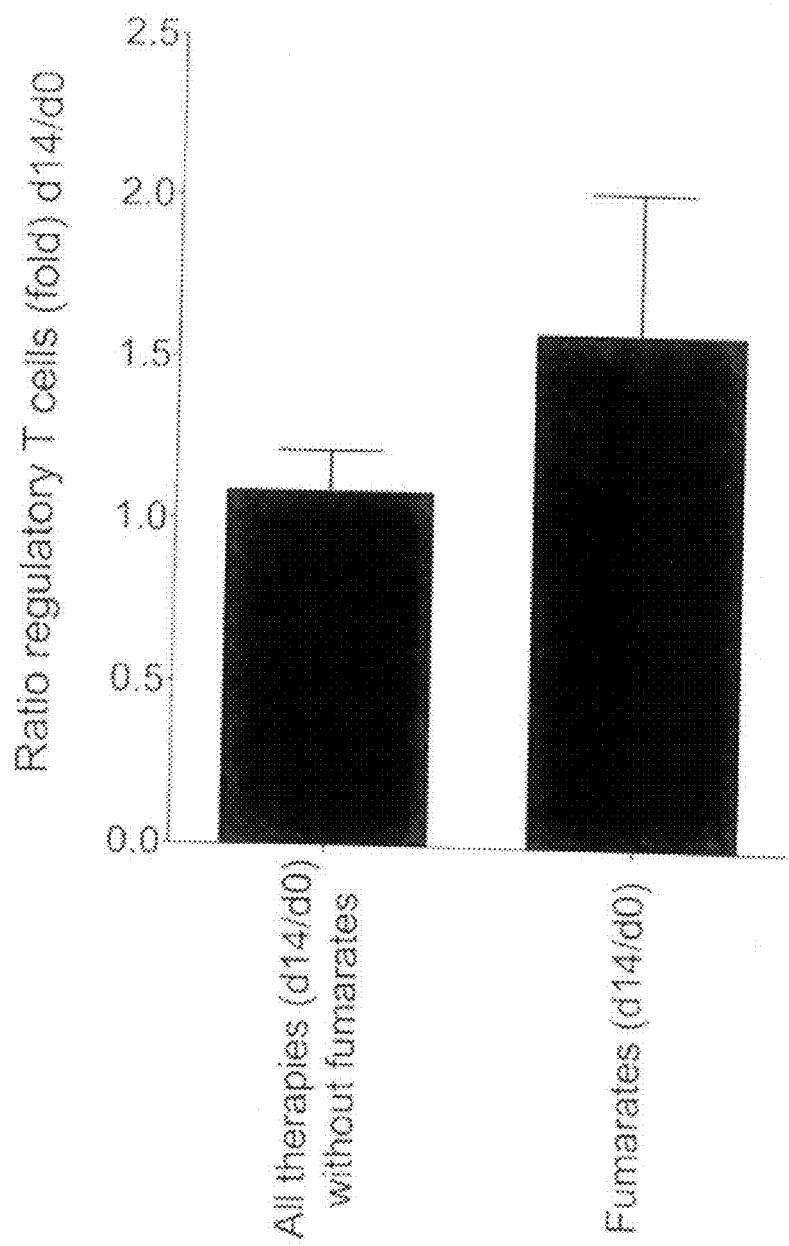
FIG. 6 shows a comparison of the ratio of Treg cells after administration of 2×0.5 g sodium propionate together with fumarates for the treatment of MS in the standard dose before and after 14 days of treatment.

In studies with MS patients it is shown that the combined administration of fumarates (2×120 or 240 mg per day) and sodium propionate (2×0.5 g per day) results in-a significant increase in Treg cells by a factor of 1.6 (see FIG. 6). In comparison, other commonly used drugs for the treatment of MS together with sodium propionate only showed an increase by a factor of 1.1. The disproportionate increase in the amount of Treg cells signifies a corresponding reduction in the autoimmune response. Fumarates and short-chain fat carboxylates work together synergistically.

The invention also relates to the use of 03-8 carboxylic acids, their physiologically acceptable salts and esters with 01-8 alkyl alcohols together with fumaric acid esters and their salts and optionally vitamin B12 as immunomodulators useful for treating autoimmune-related diseases. These combinations may also be used to produce drugs intended to accompany the therapy for autoimmune diseases, and also as a dietary supplement having immunomodulating activity.

The inventive acids, in particular propionic acid and butyric acid have an influence on the intestinal physiology and the microbiome present there. In this way, they have an impact on the composition of the microbiome. The number of bacteria degrading propionate and butyrate increases significantly while at the same time the normal intestinal microbiota are only slightly affected. In contrast, long-chain carboxylic acids (lauric acid) cause the number of Provotellaceae and some families of Phylum Bacteroidetes present in mice to reduce significantly.

The relationship of metabolic syndrome with inflammatory diseases, particularly MS and psoriasis is a topic among experts. Metabolic syndrome is usually accompanied by a disorder of the intestinal microbiome. Propionate is conducive to counteracting such disorders and correcting abnormalities of the intestinal microbiome.

For the treatment of chronic inflammatory conditions and skin, the carboxylic acids and their esters and salts as used in the invention can be combined with other commonly used agents.

Accordingly, the invention also relates to the use of $C_3$-$C_8$ carboxylic acids, their physiologically acceptable salts and esters with $C_{1-8}$ alkyl alcohols in combination with fumaric acid esters and their salts and vitamin B12 as immunomodulators useful for treating MS and psoriasis.

It is recognized that the topical and oral application of propionic acid and propionates are largely equivalent with regards to their physiological effects. The studies in mice described below where fatty acids or salts thereof have been administered orally also allows for conclusions to be drawn about their topical application.

In mice treated with propionic acid, the number of regulatory T cells increases with the changes that occur in the microbiota (CD4+CD25+ Foxp3+ Treg). Gene expression profiling of signature cytokines showed increased values with respect to TGFβ1, IL-10—generally anti-inflammable messengers—and Foxp3 in propionic acid-fed mice with experimental autoimmune encephalomyelitis (EAE).

Moreover, the aliphatic chain length of the carboxylic acids also affects the Th1/Th7-mediated autoimmunity as well as the regulatory response of Treg in an in vivo mouse model. Mice fed a lauric acid enriched diet showed in the EAE model a significant reduction of TH1 and TH17 cells in the small bowel and at the same time an accumulation of Th1/Th17 in the central nervous system which suggests that the control of the inflammatory cells has been transferred from the bowel to the brain/spinal marrow. Under otherwise similar conditions, propionic acid caused a significant increase of TGFβ1, IL-10, and Foxp3. These results taken together and in comparison to a control group, showed a change towards worsening following the onset of the induced disease in the MS mouse model with a diet comprising long-chain fatty acids, whereas in mice that were prophylactically given propionic acid a significant improvement was observed. In this context, MS and psoriasis are to be regarded as largely similar.

As a result, propionic acid appears to be able to change and normalize a compromised balance occurring between Treg and effector T cells (Th1/Th17 Psoriasis patients show such a disturbed balance).

EXAMPLES

Experimental Findings

Mice kept under standardized conditions were fed on a normal diet enriched with long-chain fatty acids (30.9% lauric acid) and with 200 µl of propionate daily administered orally. The propionate was given either at the time of disease induction (DI) or at the onset of the disease (OD).

For the induction of EAE the mice were anesthetized and administered two subcutaneous injections of a 50 µl emulsion applied to the left and right tail basis and comprising a total of 200 µg $MOG_{35-55}$ (myelin oligodendrocyte glycoprotein) and 200 µg Freund's adjuvant (CFA) with 4 mg/ml of *M. tuberculosis*. Pertussis toxin (200 mg/mouse) was given intraperitoneally on day 0 and day 2 after the induction. The clinical assessment took place on a daily basis using a 5-point scale (SEM). The assessment was as follows:

0=normal
1=Tail paralysis impairing raising
2=Gait ataxia
3=Paraparesis of hind legs
4=Tetraparesis
5=Death Mice showing SEM 4 or 5 were excluded.
Results are shown in the Figures.

Example 1

FIG. 1 shows results of a mouse population fed a diet enriched with lauric acid in comparison to a control group. Onset of the disease occurred approximately ten days after induction with the disease reaching its peak after seventeen days. With respect to SEM scores the control group scored better than the group fed the diet enriched with lauric acid.

Example 2

Figure 2:
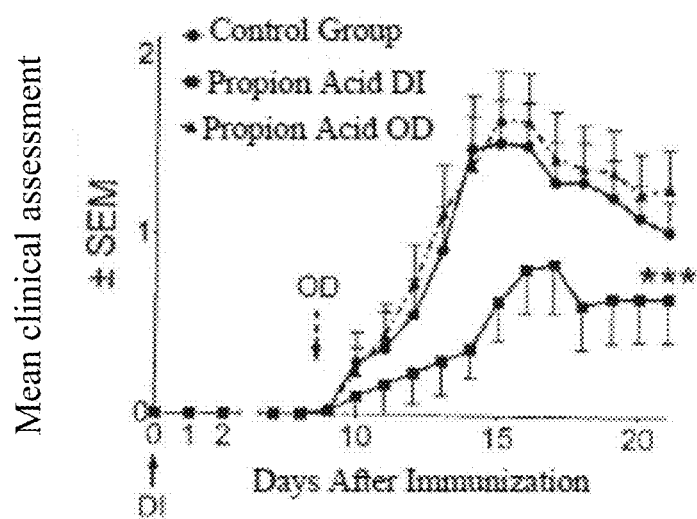
FIG. 2 is a graph showing the effect of a propionic acid diet initiated at the time of disease induction (DI) or at the time of onset of symptoms (OD) compared to a control group on SEM in the mouse EAE model.

FIG. 2 shows a results of a comparison of mouse population fed with propionic acid diet versus a control group. The propionic acid was administered either on the day of induction (DI) or on the day of onset of disease occurred (OD). It was found that the group that was given propionic acid on the day the onset of disease occurred (OD) showed a significantly less favorable disease progression than the control group.

Figure 3:
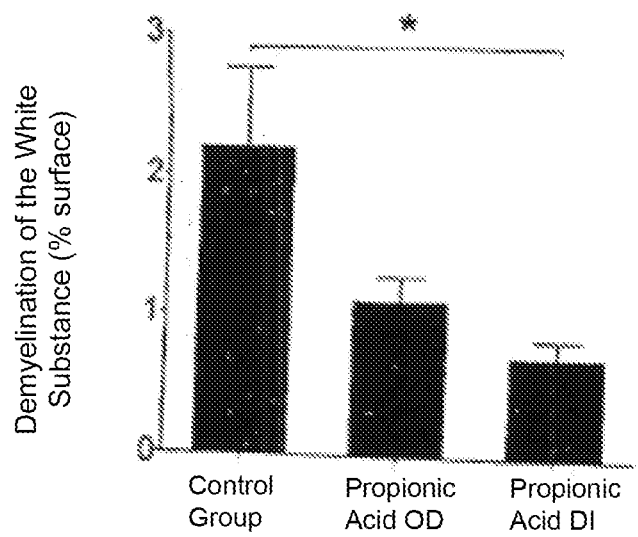
FIG. 3: is a graph showing the effect of propionic acid diet initiated at the time of disease induction (DI) or at the time of onset of symptoms (OD) compared to a diet control group on relative axonal density, demyelination in the white matter, and CD3+ cells in the mouse EAE model.
Figure 3:
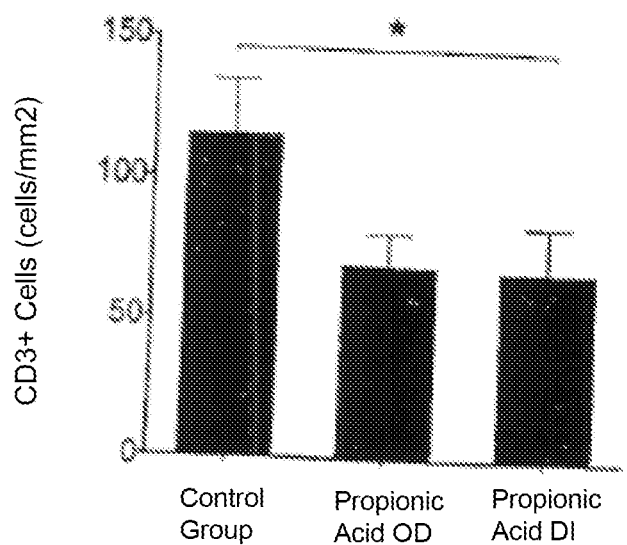

The influence of the propionic acid on the relative axonal density, the demyelination of the white matter, and the number of CD3+-cells is shown in FIG. 3. In general, the administration of propionic acid results in a significant improvement of the condition compared to the control group.

Figure 4:
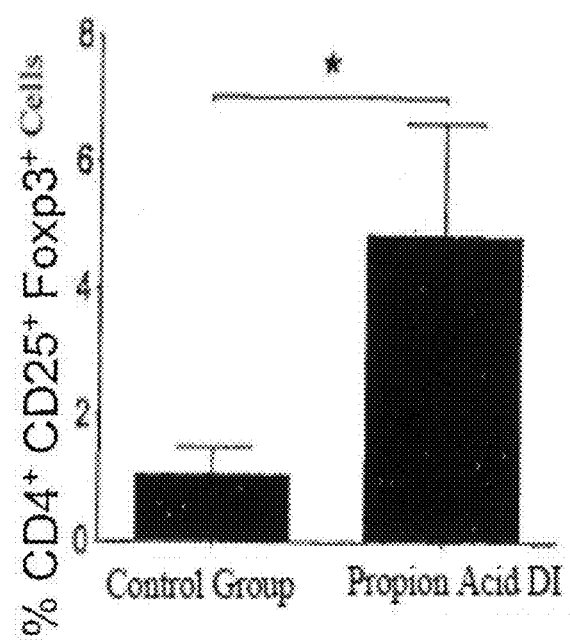
FIG. 4: is a graph showing the effect of propionic acid diet initiated at the time of disease induction (DI) compared to a control group on levels of CD4+CD25+ Foxp3 cells in mouse EAE model

FIG. 4 shows the effect of administration of propionic acid on the CD4+–CD25+ Foxp3 cells expressed as a significant increase in comparison to the control group.

Example 3

Figure 5:
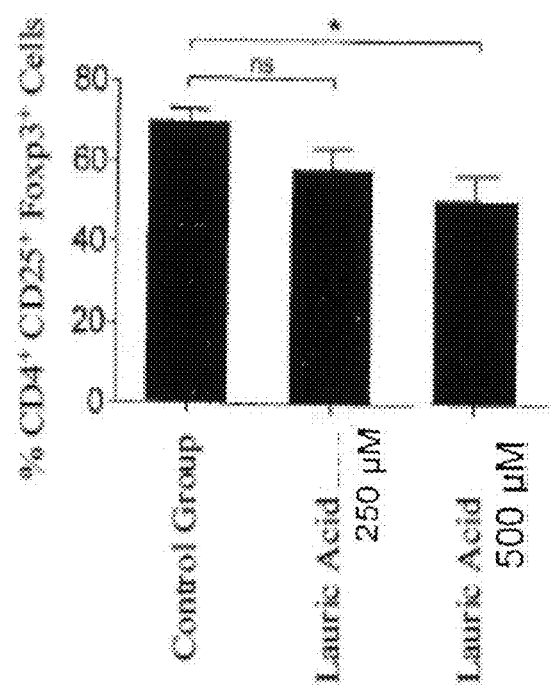
FIG. 5 is a graph showing the effect of lauric acid diet (250 μM and 500 μM) initiated at the time of disease induction (DI) compared to a control group on levels of CD4+CD25+ Foxp3 cells in mouse EAE model.

FIG. 5 shows the effect of a lauric acid enriched diet on the CD4+CD25+ Foxp3 cells in comparison to a control group. The administration of the long-chain fatty acids leads to a reduction in T cells compared to the control value. The percentage reduction was dependent on the concentration of the long-chain fatty acids.

Example 4

FIG. 6 shows a comparison of the ratio of Treg cells after ad ministration of 2×0.5 g sodium propionate in combination with established agents (see below) for the treatment of MS in the usual dose before and after 14 days of treatment.

For the combination of sodium propionate and dimethyl fumarate (2×120 or 240 mg daily), the number of Treg cells increased by a factor of 1.6. In a comparison group treated with the patient-specific dose of interferon beta (Betaferon, Rebif 22), glatiramer acetate, teriflunomide or fingolimod together with the above stated amount of sodium propionate, the number of Treg cells increased by a factor of 1.1.

The invention claimed is:

1. A pharmaceutical composition for treating multiple sclerosis, psoriasis, and/or rheumatoid arthritis in a subject in need thereof, comprising one or more $C_3$-$C_8$ carboxylic acids, physiologically acceptable salts and/or esters thereof, and one or more fumaric acid esters and/or physiologically acceptable salts thereof, wherein the one or more $C_3$-$C_8$ carboxylic acids are propionic acid and/or butyric acid.

2. The pharmaceutical composition of claim 1, wherein the $C_3$-$C_8$ carboxylic physiologically acceptable salts are salts of sodium, potassium, magnesium, calcium, zinc, and/or iron.

3. The pharmaceutical composition of claim 2, wherein the $C_3$-$C_8$ carboxylic acid salt is sodium propionate and/or calcium propionate.

4. The pharmaceutical composition of claim 1, wherein the fumaric acid esters and/or physiologically acceptable salts thereof comprise fumaric acid dimethyl ester and/or the physiologically acceptable salts of fumaric acid monomethyl ester.

5. The pharmaceutical composition of claim 1, wherein the fumaric acid esters and/or physiologically acceptable salts thereof comprise a mixture of fumaric acid dimethyl ester and salts of fumaric acid monomethyl ester.

6. The pharmaceutical composition of claim 1, wherein the fumaric acid esters and/or physiologically acceptable salts thereof comprise a mixture of dimethyl fumarate and the calcium, magnesium, and/or zinc salts of ethyl fumarate.

7. The pharmaceutical composition of claim 1 wherein said composition is formulated for oral administration in a single dosage form comprising the one or more $C_3$-$C_8$ carboxylic acids, physiologically acceptable salts and/or esters thereof, and one or more fumaric acid esters and/or physiologically acceptable salts thereof, or in multiple dosage forms wherein each of the multiple dosage form comprises either the $C_3$-$C_8$ carboxylic acids, physiologically acceptable salts and/or esters thereof, or the one or more fumaric acid esters and/or physiologically acceptable salts thereof.

8. The pharmaceutical composition of claim 7 wherein said composition is formulated in multiple dosage forms wherein each multiple dosage form comprises either the $C_3$-$C_8$ carboxylic acids, physiologically acceptable salts and/or esters thereof, or the one or more fumaric acid esters and/or physiologically acceptable salts thereof.

9. The pharmaceutical composition of claim 7, wherein the single dosage form or the multiple dosage forms are capsules or tablets.

10. The pharmaceutical composition of claim 9, where the capsules or tablets are encapsulated in a blister pack.

11. The pharmaceutical composition of claim 1, wherein the one or more $C_3$-$C_8$ carboxylic acids, physiologically acceptable salts and/or esters thereof, is sodium propionate, and the one or more fumaric acid esters and/or physiologically acceptable salts thereof is dimethyl fumarate, salts of fumaric acid monomethyl ester, and/or salts of fumaric acid monoethyl ester.

12. The pharmaceutical composition of claim 1, further comprising vitamin A, vitamin B12, and/or vitamin D.

13. The pharmaceutical composition of claim 1, further comprising cyclodextrin.

14. A pharmaceutical composition for treating multiple sclerosis, psoriasis, and/or rheumatoid arthritis in a subject in need thereof, comprising about 0.1 g to about 1.0 g of one or more $C_3$-$C_8$ carboxylic acids, physiologically acceptable salts and/or esters thereof, and about 0.02 g to about 0.4 g of one or more fumaric acid esters and/or physiologically acceptable salts thereof, wherein the one or more $C_3$-$C_8$ carboxylic acids are propionic acid and/or butyric acid.

15. The pharmaceutical composition of claim 14, wherein the one or more $C_3$-$C_8$ carboxylic acids, physiologically acceptable salts and/or esters thereof, is sodium propionate, and the one or more fumaric acid esters and/or physiologically acceptable salts thereof is dimethyl fumarate, salts of fumaric acid monomethyl ester, and/or salts of fumaric acid monoethyl ester.

16. The pharmaceutical composition of claim 14 wherein said composition is formulated for oral administration in a single dosage form comprising the one or more $C_3$-$C_8$ carboxylic acids, physiologically acceptable salts and/or esters thereof, and one or more fumaric acid esters and/or physiologically acceptable salts thereof, or in multiple dosage forms wherein each multiple dosage form comprises either the $C_3$-$C_8$ carboxylic acids, physiologically acceptable salts and/or esters thereof, or the one or more fumaric acid esters and/or physiologically acceptable salts thereof.

17. The pharmaceutical composition of claim 14, wherein said composition is formulated in multiple dosage forms wherein each multiple dosage form comprises either the $C_3$-$C_8$ carboxylic acids, physiologically acceptable salts and/or esters thereof, or the one or more fumaric acid esters and/or physiologically acceptable salts thereof.

18. The pharmaceutical composition of claim 16, wherein the $C_3$-$C_8$ carboxylic acids, physiologically acceptable salts and/or esters thereof, further comprise a cyclodextrin admixture.

19. The pharmaceutical composition of claim 16, wherein the $C_3$-$C_8$ carboxylic acids, physiologically acceptable salts and/or esters thereof, further comprise vitamin B12.

20. A dietary supplement for treating multiple sclerosis, psoriasis, and/or rheumatoid arthritis in a subject in need thereof, comprising one or more $C_3$-$C_8$ carboxylic acids, physiologically acceptable salts and/or esters thereof, and one or more fumaric acid esters and/or physiologically acceptable salts thereof, wherein the one or more $C_3$-$C_8$ carboxylic acids are propionic acid and/or butyric acid.

* * * * *